US006770023B2

(12) United States Patent
Vaiser et al.

(10) Patent No.: US 6,770,023 B2
(45) Date of Patent: Aug. 3, 2004

(54) GENERATOR OF ELECTRIC AND MAGNETIC FIELDS, A CORRESPONDING FIELD DETECTOR, AND A SAMPLE ANALYZER AND TREATMENT APPARATUS INCORPORATING THE FIELD GENERATOR AND/OR FIELD DETECTOR

(75) Inventors: Leonid Vladimirovich Vaiser, Budapest (HU); Boris Ivanovich Kokorin, Winchester (GB)

(73) Assignee: HEX Technology Holdings Limited, Jersey (GB)

( * ) Notice: Subject to any disclaimer, the term of this patent is extended or adjusted under 35 U.S.C. 154(b) by 0 days.

(21) Appl. No.: 10/396,440

(22) Filed: Mar. 26, 2003

(65) Prior Publication Data

US 2003/0169132 A1 Sep. 11, 2003

Related U.S. Application Data

(60) Division of application No. 08/949,760, filed on Oct. 14, 1997, now Pat. No. 6,552,530, which is a continuation-in-part of application No. 08/586,909, filed as application No. PCT/HU93/00043 on Jul. 27, 1993, now abandoned.

(51) Int. Cl.[7] .................................................. A61N 1/00
(52) U.S. Cl. ........................................................ 600/13
(58) Field of Search ....................................... 600/9–15

(56) References Cited

U.S. PATENT DOCUMENTS

| | | | |
|---|---|---|---|
| 3,789,832 A | 2/1974 | Damadian | |
| 4,622,558 A | 11/1986 | Corum | |
| 4,751,515 A | 6/1988 | Corum | |
| 5,339,061 A | 8/1994 | Reick | |
| 5,442,369 A | 8/1995 | Voorhies et al. | |
| 5,504,341 A | 4/1996 | Glavish | |
| 5,654,723 A | 8/1997 | Craven et al. | |
| 6,179,772 B1 * | 1/2001 | Blackwell | 600/13 |
| 6,239,760 B1 | 5/2001 | Van Voorhies | |

FOREIGN PATENT DOCUMENTS

| | | |
|---|---|---|
| DE | 23 04 500 | 8/1974 |
| DE | 23 06 922 | 8/1974 |
| DE | 24 23 399 | 2/1977 |
| DE | 26 34 628 | 2/1977 |
| DE | 27 48 780 | 5/1978 |
| EP | 0 011 019 | 5/1980 |
| EP | 0 136 530 | 4/1985 |
| EP | 0 500 983 | 9/1992 |
| HU | 187 898 | 1/1988 |
| HU | 195 939 | 1/1989 |
| HU | 205 042 | 3/1992 |

OTHER PUBLICATIONS

Sadiku, Matthew N.O. and Demarest, Kenneth, "Wave Propagation", The Electrical Engineering Handbook, Ed. Richard C. Dorf, Chapter 35, pp. 837–860 (1993).

* cited by examiner

*Primary Examiner*—John P. Lacyk
(74) *Attorney, Agent, or Firm*—Finnegan, Henderson, Farabow, Garrett, & Dunner, L.L.P.

(57) ABSTRACT

A field generator/detector including at least one super-toroidal conductor and a device to energize the super-toroidal conductor to generate varying electric and magnetic fields. Where conductor has a length l, the super-toroidal conductor is energized with at least one frequency component equal to or greater than 2c/l, where c is the speed of light in free space. Then the near field generated at this frequency close to the super-toroidal conductor has a strongly inhomogeneous spatial distribution similar or more complex than that generated by four or more electric charges and/or current loops. At any particular moment in time, the amplitudes of the electric and magnetic fields components of such a complex field change significantly over a distance comparable with the smallest winding feature of the super-toroidal conductor. The field generator/detector may be used in a sample analyzer having a chamber and a sample holder within the chamber. The chamber contains at least a first super-toroidal conductor having at least the length l. This super-toroidal conductor is energized to generate oscillating electric and magnetic field in the region of a sample in the chamber. The response of the generated field to the presence of a sample on the sample holder is determined, so that an analysis can be made. The field generator/detector may used also as a treatment apparatus for treating a desired component of a specimen. The treatment super-toroidal conductor is energized at a frequency or set of frequencies or continuous band of frequencies greater than 2c/l to produce strongly inhomogeneous electric and magnetic fields.

6 Claims, 17 Drawing Sheets

10
11
12
13
15
16
17
14

GENERATOR OF ELECTRIC AND MAGNETIC FIELDS, A CORRESPONDING FIELD DETECTOR, AND A SAMPLE ANALYZER AND TREATMENT APPARATUS INCORPORATING THE FIELD GENERATOR AND/OR FIELD DETECTOR

CROSS REFERENCE TO RELATED APPLICATION

This application is a division of U.S. application Ser. No. 08/949,760, filed Oct. 14, 1997 now U.S. Pat. No. 6,552, 530, which is a continuation-in-part of Application Ser. No. 08/586,909, filed May 13, 1996, now abandoned, which is a §371 of PCT/HU93/00043 dated Jul. 27, 1993.

TECHNICAL FIELD OF INVENTION

The invention relates to a generator of electric and magnetic fields, particularly incorporating a super-toroidal conductor. The invention also relates to a corresponding detector of electric and magnetic fields and to a sample analyzer and treatment apparatus incorporating the field generator and/or detector.

BACKGROUND ART OF THE INVENTION

The use of toroidal windings as electromagnetic radiating antennas is known, e.g. from U.S. Pat. Nos. 4,622,558, 4,751,515, 5,442,369 and 5,654,723. However, none of these prior patents contemplate the use of a super-toroidal winding for generating an electromagnetic field. Further, the last two patents are particularly concerned with ensuring that a toroidal antenna can be designed to operate at a particular frequency to produce an electromagnetic field, equivalent to that produced by classic electric or magnetic dipole antennas.

DISCLOSURE OF THE INVENTION

An object of the present invention is the generation of a varying electric and magnetic fields using a super-toroidally wound conductor. In this context, a super-toroidal conductor is one in which the windings of a toroidally wound conductor are constituted by helical windings. Further explanation of super-toroidal conductors of various orders will be given later herein. Another object of the present invention is the generation of periodically varying electric and magnetic fields with strong spatial inhomogeneousity, that is fields with high spatial gradients of the field's amplitudes by comparison with the typical dipole electric or magnetic field produced by a radiating antenna. A further object of the present invention is the detection of electric and magnetic fields of this kind using a super-toroidal conductor as a detecting element.

A still further object of the present invention is the analysis of samples using strongly inhomogeneous fields generated by super-toroidal conductors.

A still further object of the present invention is the treatment of specimens using such strongly inhomogeneous periodically varying fields.

Accordingly, the present invention provides a field generator comprising at least one super-toroidal conductor and means to energize the super-toroidal conductor to generate varying electric and magnetic fields. Where conductor has a length l, the super-toroidal conductor should be energized with at least one frequency component equal to or greater than 2c/l, where c is the speed of light in free space. Then the near field generated at this frequency close to the super-toroidal conductor will have a strongly inhomogeneous spatial distribution similar or more complex than that generated by four or more electric charges and/or current loops. At any particular moment in time, the amplitudes of the electric and magnetic fields components of such a complex field change significantly over a distance comparable with the smallest winding feature of the super-toroidal conductor. Such a strongly inhomogeneous field can be distinguished from the classic electromagnetic fields produced in the prior art.

The invention also provides a detector for electric and magnetic fields comprising at least one super-toroidal conductor and means responsive to electrical currents generated in said conductor by varying electric and magnetic fields.

Examples of the invention provide a sample analyzer comprising a chamber, and a sample holder within the chamber. The chamber contains at least a first super-toroidal conductor having at least the length l. This super-toroidal conductor is energized to generate oscillating electric and magnetic field in the region of any sample on the sample holder. The electromagnetic field varies with a frequency component equal to or greater than 2c/l to produce a strongly spatial inhomogeneous field. Then the response of the generated field to the presence of a sample on the sample holder is determined, so that an analysis can be made.

The invention also provides treatment apparatus for treating a desired component of a specimen. The apparatus comprises a treatment super-toroidal conductor having a length l. The treatment super-toroidal conductor is energized at a frequency or set of frequencies or continuous band of frequencies greater than 2c/l to produce strongly inhomogeneous electric and magnetic fields. The specimen is exposed to this field and the frequency or set of frequencies or continuous band of frequencies is selected to provide the required treatment of the desired component of the specimen. In order to select the required frequency or set of frequencies or continuous band of frequencies for treatment, a sample corresponding to the desired component of the specimen to be treated may be analyzed in the above described sample analyzer. The treatment frequency or set of frequencies or continuous band of frequencies is then selected in accordance with the response determined in the sample analyzer. In this way, treatment of predominantly or only selected components of a specimen can be ensured by incorporating a sample of the desired component in the associated sample analyzer.

For treatment purposes the electromagnetic field may be modulated by a low frequency signal within a band of from 0.001 to 1000 cycles per second.

Examples of the present invention will now be described with reference to the following drawings.

DESCRIPTION OF THE PREFERRED EMBODIMENTS

Figure 1A:
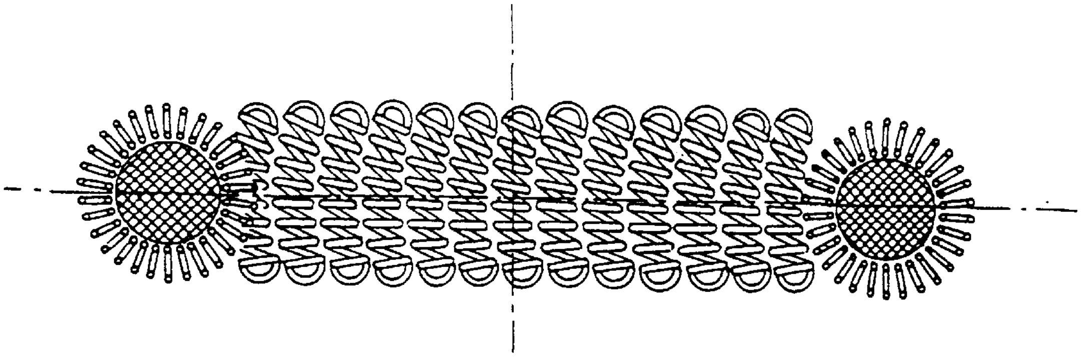
FIGS. 1*a*, 1*b*, and 1*c* show designs of a super-toroidal conductor for use in the invention.
Figure 1B:
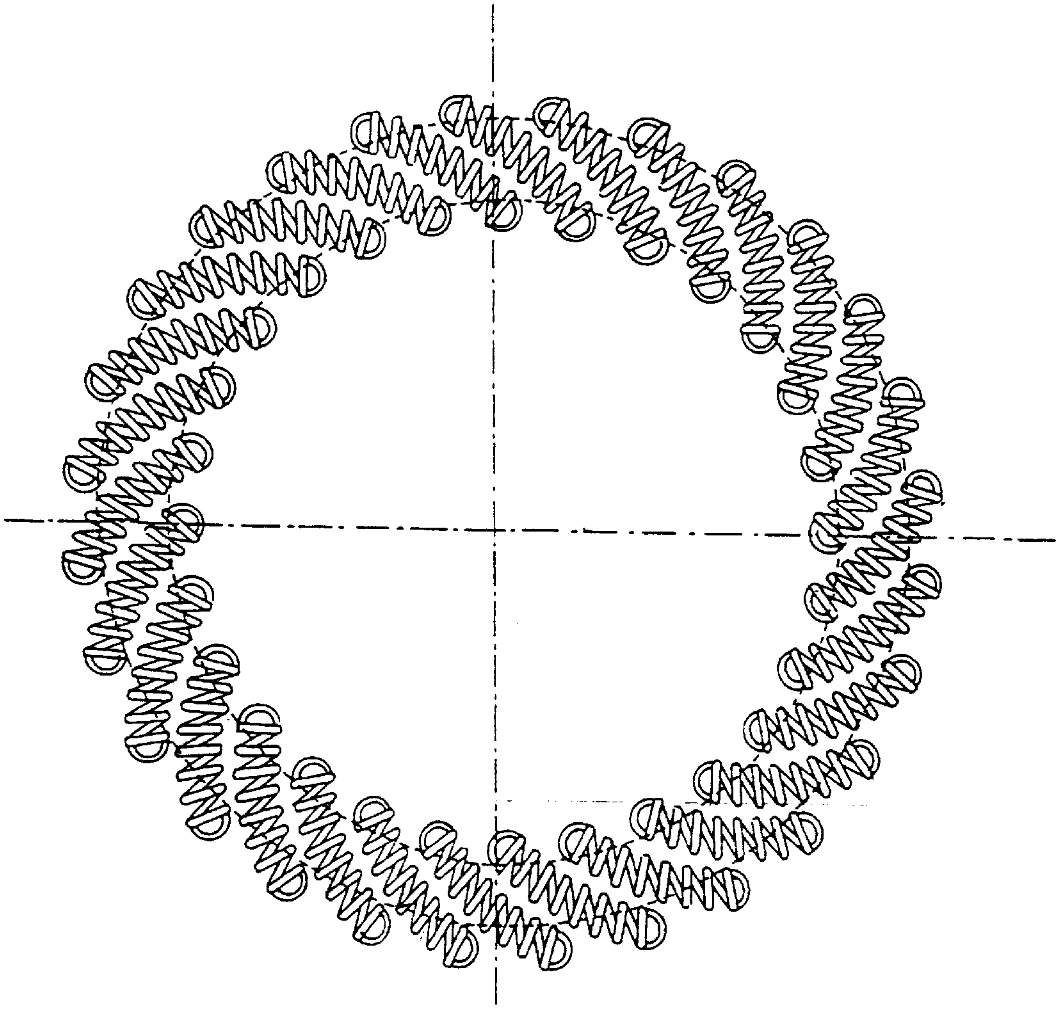
Figure 1C:
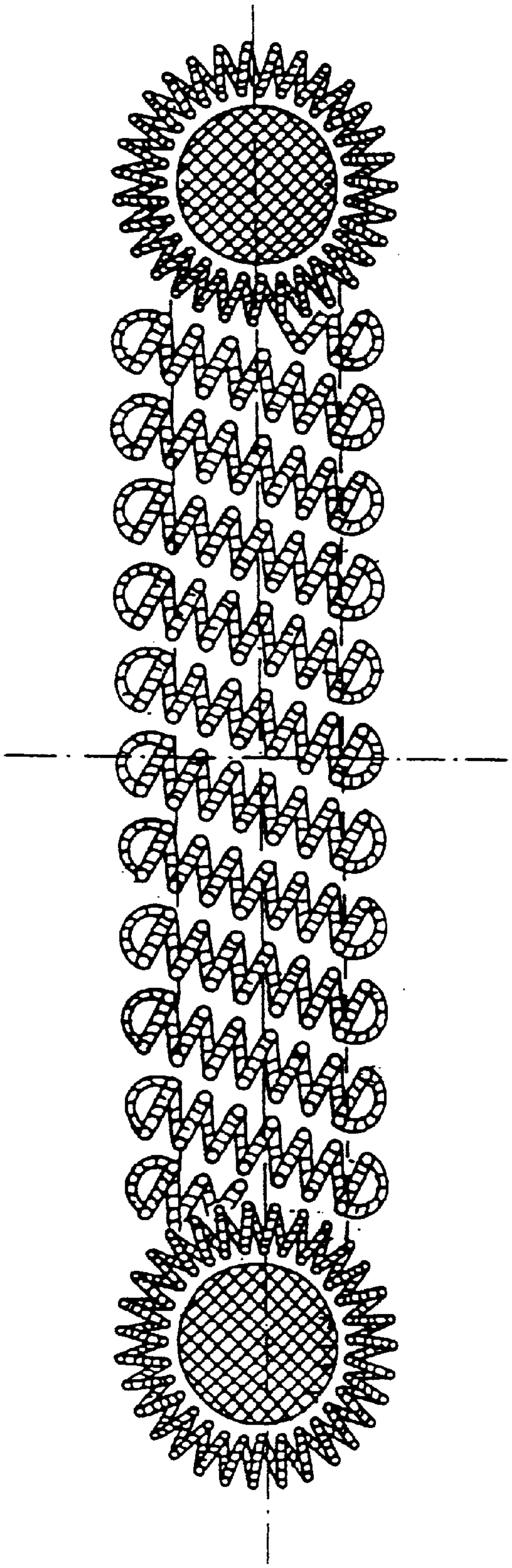

The super-toroidally wound conductor shown in FIGS. 1*a* to 1*c* is an example of field generator for effecting the method proposed in the invention.

A toroidal winding comprises a conductor wound helically around a toroidal former. In a first order super-toroidal winding, the conductor of the toroidal winding is replaced by a long helically coiled conductor which is itself wound around the toroidal former. In a second order super-toroidal winding, the conductor of the first order super-toroidal winding is itself wound into a long helically coiled conductor. In a third order super-toroidal winding, the conductor of the second order super-toroidal winding is itself wound into a long helically coiled conductor, and so forth up to higher orders. In the examples of the present invention to be described below, super-toroidal windings of second and third order are included.

In practice it is possible to make super-toroidal of the twelfth or even the fifteenth order.

In general, one or more such super-toroidal conductors are energized to produce an electromagnetic field having two different frequencies: a high frequency component in the band from 1 kHz to 1000 GHz modulated by a low frequency component between 0.001 lines and 100 Hz.

Efficiency of operation can improve, if the low and frequency modulating signal is chopped at a predetermined phase angle. Experience shows that to provide a field having a stimulating effect on a sample, the low frequency modulating signal should be chopped at a phase angle $0.33\times2\pi$, and to provide a field having an inhibiting effect, the low frequency signal should be chopped at a phase angle$\times2\pi$.

Figure 2:
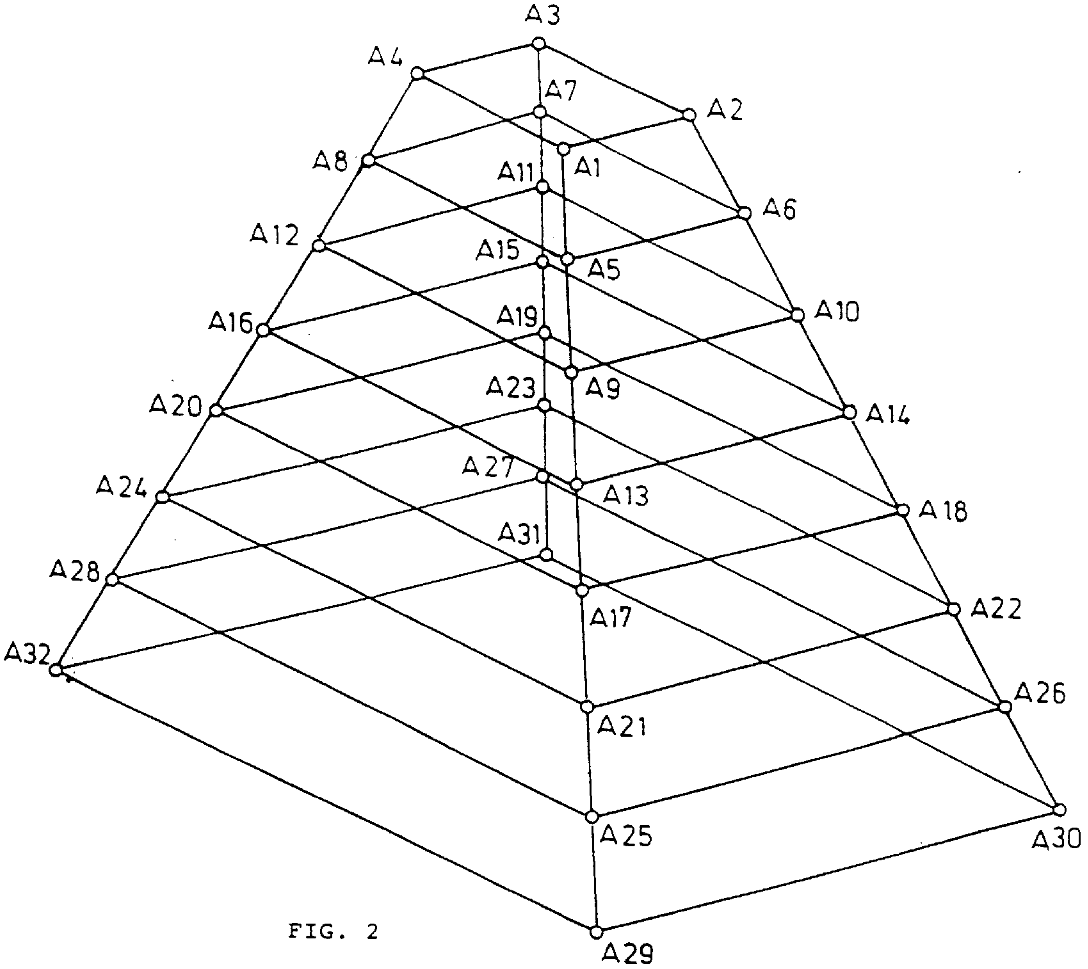
FIG. 2 is a perspective view of an enclosure which may embody the present invention, either for sample analysis or specimen treatment.

FIG. 2 is an external view of an enclosure used in a sample analyzer embodying the present invention. The enclosure comprises a box 10 having a removable lid 11 constituting one face of the box. A hatch 12 is provided in the lid for easy access to the interior of the enclosure. The enclosure is made of metal and is intended to provide electromagnetic screening of the interior of the box. Feedthroughs 13 are provided for electrical signals through a front face 14 of the box and include coaxial electrical sockets 15 for selective engagement with corresponding coaxial plugs 16 on coaxial connecting cables 17.

Figure 3:
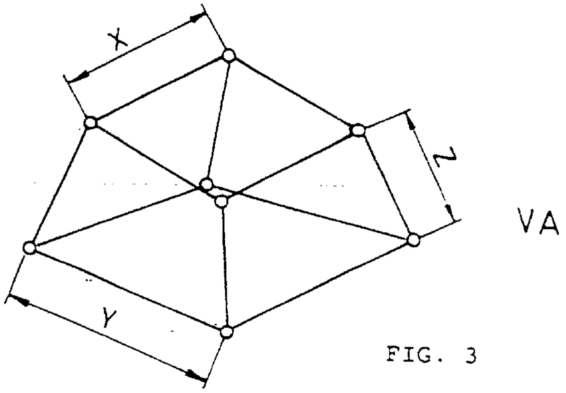
FIG. 3 is a plan view of the interior of the enclosure of FIG. 2.

FIG. 3 illustrates the interior of the box 10 with the lid 11 removed. The box contains four super-toroidal conductor assemblies 20, 21, 22 and 23. The toroidal conductor assemblies 20 and 21 are mounted on respective dielectric mounting blocks 24 and 25, so as to be essentially parallel to opposite upright end faces 26 and 27 of the box 10.

Substantially midway between the toroidal assemblies 20 and 21 a sample tray 28 is mounted on the bottom face of the box 10. Sample tray 28 provides a flat base with an upstanding rim 29 sized so as accurately to locate a removable sample holder on the tray 28 within the box. As shown in the figure, the toroidal conductor assembly 22 is located around the base of the sample tray 28, so that any sample placed in a container upon the tray 28 lies substantially on the axis of the super-toroidal conductor 22.

The fourth super-toroidal conductor assembly 23 is mounted so as to be parallel to the rear face 30 of the enclosure, and midway between the opposed conductor assemblies 20 and 21.

Figure 4:
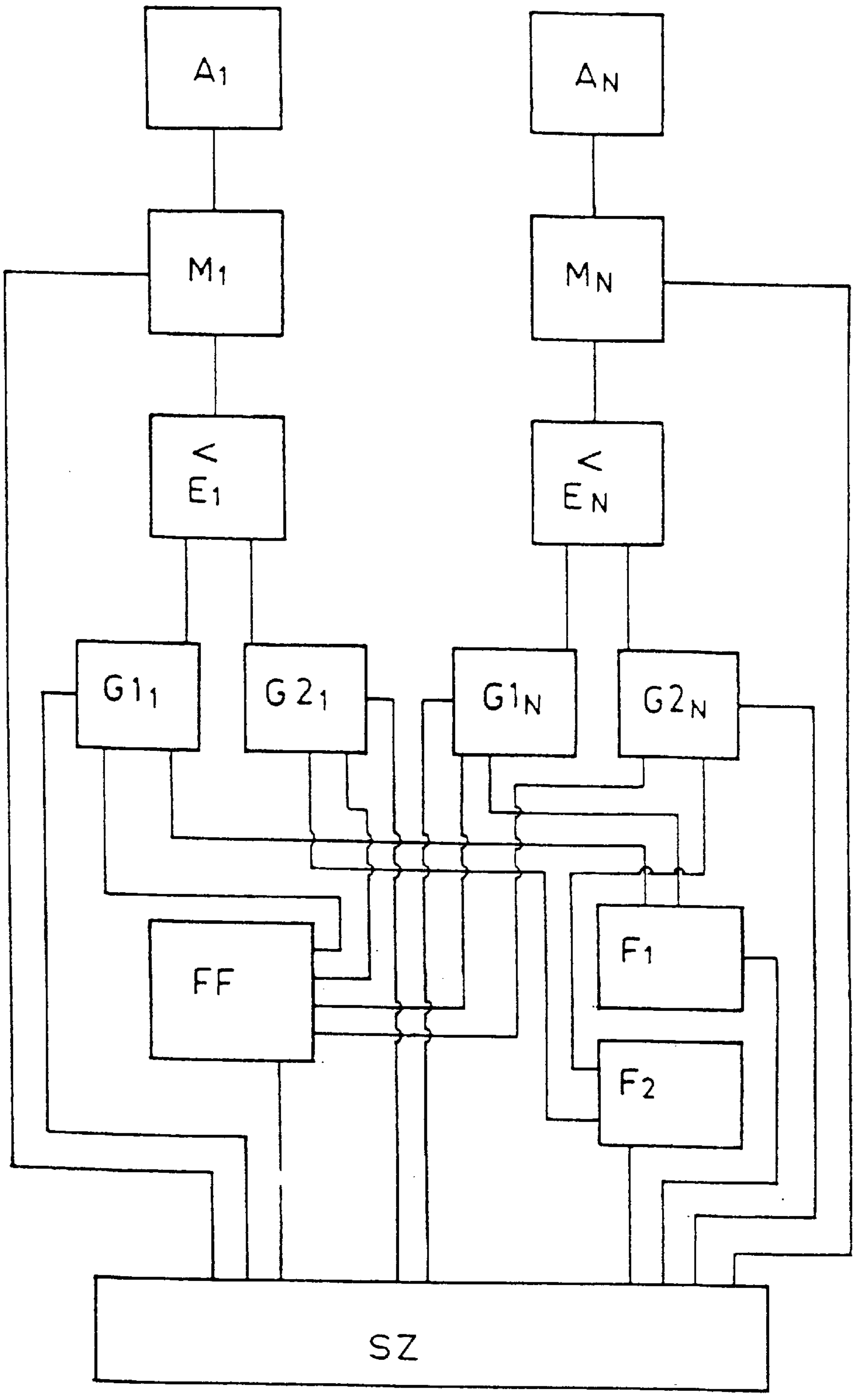
FIG. 4 is an illustration of part of a second order super-toroidal winding.

Each of the super-toroidal conductor assemblies 20 and 21 comprises a combination of a second order super-toroidal conductor and a third order super-toroidal conductor. In effect, the third order super-toroidal conductor is formed on a toroidal former constituted by a second order super-toroidal conductor. Thus, a toroidal former 31 for each of the assemblies 20 and 21 comprises a second order super-toroidal conductor such as illustrated in FIG. 4. As illustrated in FIG. 4, the second order super-toroidal conductor may be formed from a tightly wound helical spring C1 of insulated wire, which is itself then wound round in a helix C2 of greater diameter. The resulting double helical conductor C2 is then wound around the toroidal (ring shaped) former 31 to form the second order super-toroidal winding.

Figure 5:
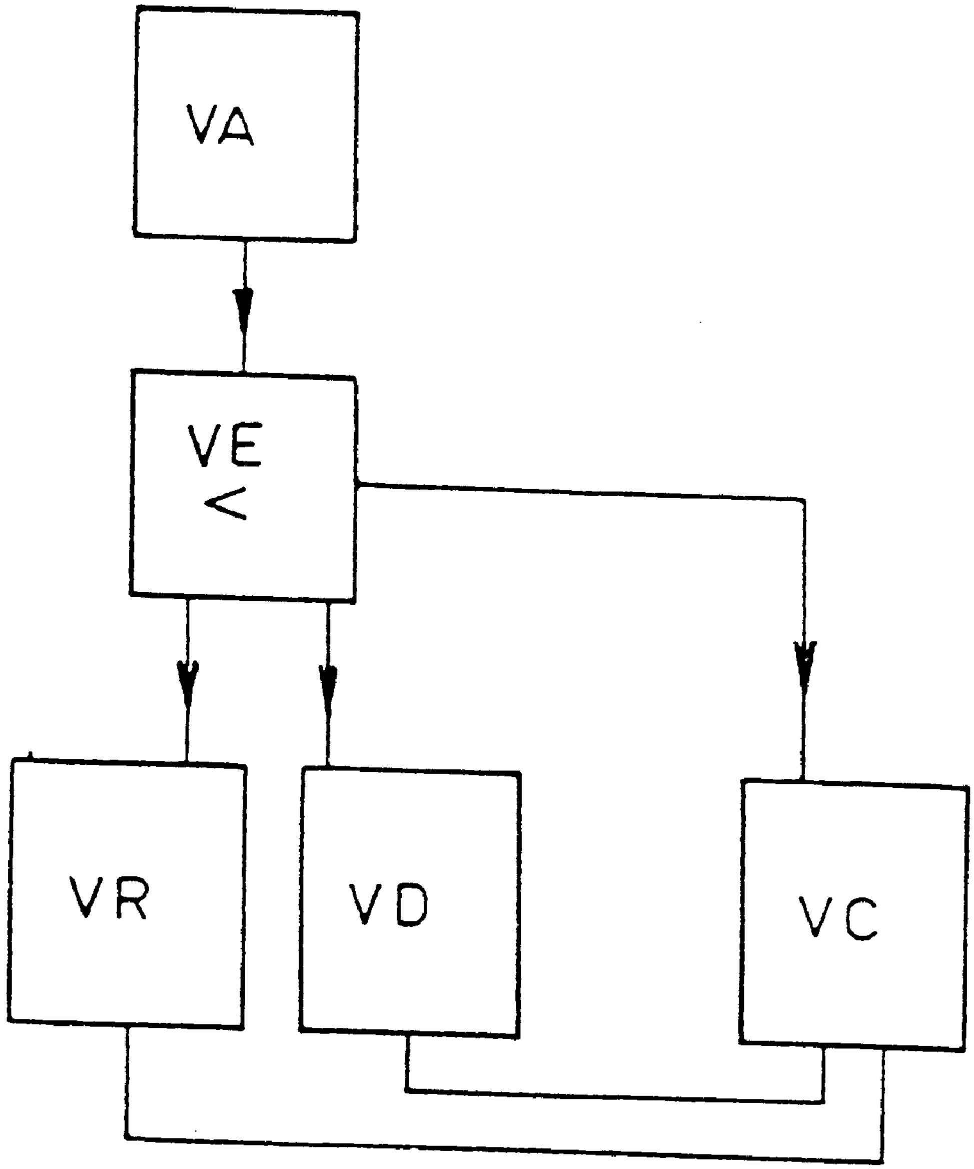
FIG. 5 is an illustration of part of a third order super-toroidal winding.

In constructing the assemblies 20 and 21, the second order super-toroidal winding is stabilised by wrapping in a heat shrinkable material and then used as the toroidal former for a third order super-toroidal winding such as illustrated in FIG. 5. The winding of FIG. 5 may be formed from a tightly wound helical spring C3 of insulated wire, which spring is itself wound into a helix C4 of greater diameter. This doubly wound helical formation C4 is then wound around a helical dielectric former F1 which is in turn wound around the toroidal former F2 of the third order super-toroidal conductor. Although not detailed in FIG. 3, in the combination of a second order super-toroidal conductor and a third order super-toroidal conductor in the assemblies 20 and 21, the toroidal former F2 in FIG. 5 is replaced by the toroidal former 31 wound by the double helical conductor C2 of FIG. 4.

The super-toroidal conductor assembly 22 comprises a simple third order super-toroidal conductor wound on a dielectric toroidal former, and the super-toroidal conductor assembly 23 is a second order super-toroidal conductor also wound on a dielectric toroidal former. The various windings of the super-toroidal assemblies within the enclosure formed by the box 10 are illustrated diagrammatically in FIG. 6 In the Figure, L1 represents the third order super-toroidal winding of super-toroidal assembly 20, and L2 represents the second order super-toroidal winding forming the toroidal former of the third order winding in assembly 20. Similarly, L6 represents the third order winding of assembly 21 on the toroidal former constituted by the second order winding L5. L3 represents the third order super-toroidal conductor winding 22 and L4 represents the second order super-toroidal conductor winding 23.

As can be seen, the outer third order winding L1 of the assembly 20 is connected in parallel with the inner second order winding L5 of assembly 21 and fed via a feedthrough 35 from the box 10 to the input of a broad band rf amplifier 36. The output of the broad band amplifier 36 is fed back through a second feedthrough 37 into the box 10 to the third order winding L3, forming the assembly 22 connected in parallel with the second order winding L4 forming the assembly 23.

The inner second order winding L2 of the assembly 20 is connected in parallel with the outer third order winding L6 of the assembly 21 and fed via a further feedthrough 38 to an analyzer 39.

With the above construction, the windings within the box 10 together with the high gain broad band radio frequency amplifier 36 form a closed loop. If the gain of the rf amplifier is sufficient, the loop gain at particular frequencies will exceed unity producing oscillation at these frequencies. Also, oscillation at other frequencies may be generated due to nonlinearity of the circuit. The frequencies at which oscillation is occurring can be monitored by the analyzer 39 which is preferably a spectrum analyzer. In a particular embodiment, the broad band radio frequency amplifier is type HP8347A from HewlettPackard and the spectrum analyzer 39 is type 8599E also from Hewlett-Packard.

It has been found that the arrangement disclosed above produces rf oscillations over a wide spectrum extending from a relatively low frequency up to 3 GHz or more. The system produces a spectrum of oscillations, detected by the analyzer 39. Depending on the tuning of the system, which may be achieved by adjustments of the positions of the super-toroidal antennas, lengths of the rf leads and the amplifier gain the spectrum has peaks at discrete frequencies over this frequency range or comprises of a combination of discrete frequencies and continuous bands of frequencies. It has been found that the distribution of these frequency peaks and/or bands is dependent on the nature of a sample material located in a container on the tray 28 in the center of the box 10. Typically, the sample may be a fluid sample and the quantity (volume) of the fluid sample and the dimensions of the container to be located on the tray 28 are maintained constant so that the features in the output spectrum dependent on the internal geometry of the enclosure 10 remain consistent for different samples.

The following example illustrates the different spectra which may be obtained from the above described instrument for different sample materials. The various samples were all liquid and were placed in identical polyethylene containers having internal diameter 30 mm, external diameter 32 mm, and height 50 mm. For each sample, the containers were completely filled.

FIGS. 7*a* and 7*b* respectively show the traces obtained from the spectrum analyzer 39 for distilled water, over the spectral regions 0 to 60 MHz and 470 to 530 MHz. The spectra were averaged over five readings each using the analyzer's built-in averaging function and then hard copied at the end of each acquisition period. As can be seen, the frequency span in each trace is 60 MHz, the analyzer resolution bandwidth is 1 KHz and the sweep time is 100 seconds. The frequency scales in all spectra are linear. The vertical scales show spectral power density of the signal in arbitrary logarithmic units.

Figure 8:
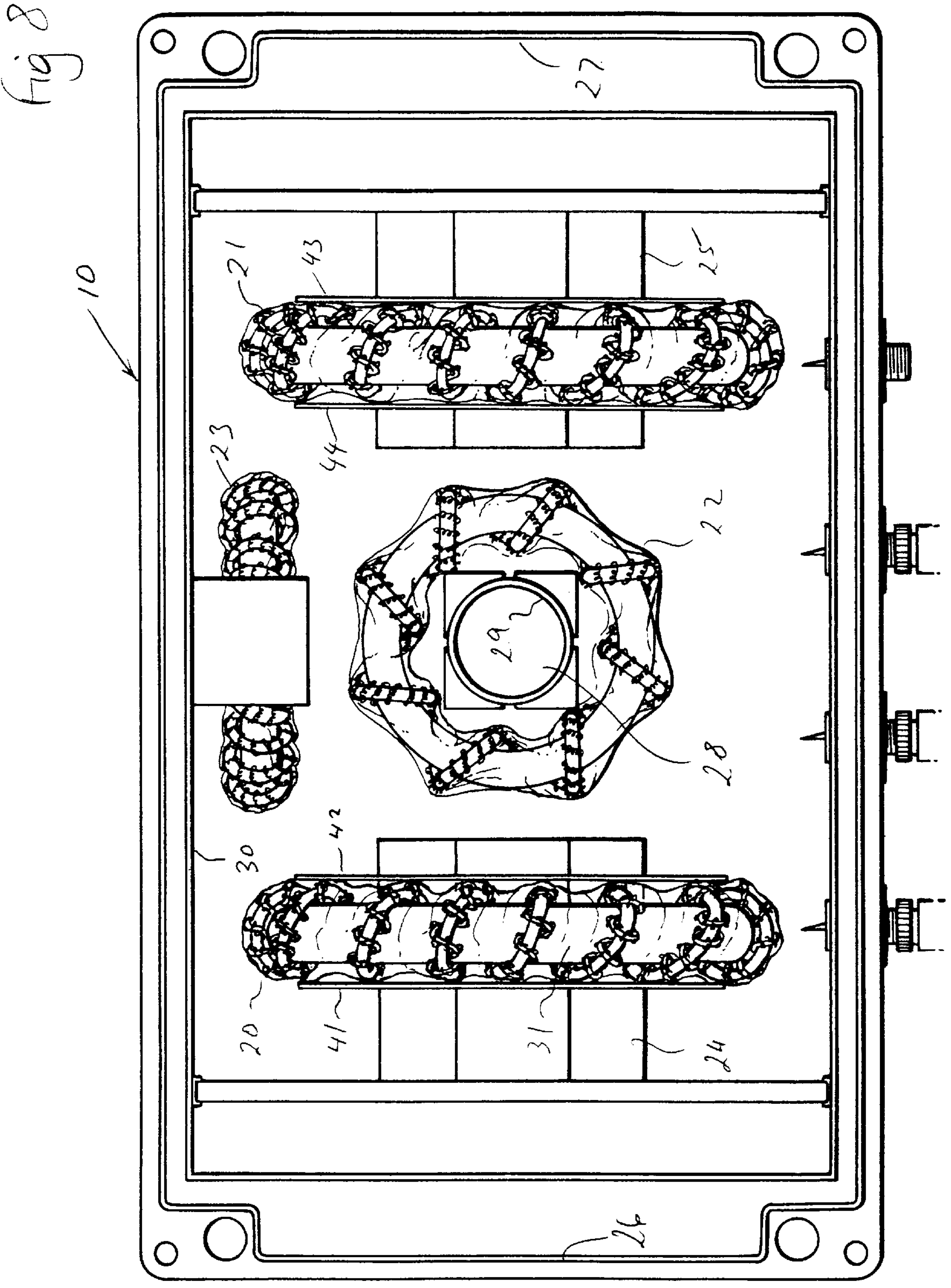
FIGS. 8*a* and 8*b* are graphical representations of the spectra at frequencies corresponding to those in FIGS. 7*a* and 7*b*, but for sea water.

FIGS. 8*a* and 8*b* show corresponding spectra at similar frequency ranges for sea water.

As can be seen by comparison of FIGS. 7*a* and 8*a*, the sea water sample has an additional line at B at about 12 MHz and a more pronounced line D at about 36 MHz. The 25 MHz line C for sea water is narrower than the equivalent for distilled water.

Comparing FIGS. 7*b* and 8*b*, sea water shows a new line B at approximately 491 MHz while line D which can be seen in distilled water appears suppressed for sea water. The sample analyzer instrument described above can therefore produce spectra which can distinguish one sample from another. By comparing the spectrum obtained for an unknown sample with a library of previously recorded spectra, the nature of an unknown sample may be determined. The comparison may be performed using correlation techniques known in the art.

More significantly, the spectrum obtained from the instrument may be used to control the electric and magnetic fields produced in a material treatment apparatus (to be described later) in such a way as to confine the effect of the electromagnetic field specifically or predominantly to a desired component in a material or body being treated.

The process going on in the above described sample analysis instrument is believed to be similar, though at radio frequencies, to the technique of inter resonator laser spectroscopy. In inter resonator laser spectroscopy, an absorbing sample to be analysed is located inside the resonator of a laser. Absorption by the sample has the effect of removing or suppressing some of the resonator modes so that the resulting spectral content of the light output from the laser is changed in a way which is specific to the nature of the absorbing substance under test. It should be understood that for this laser spectroscopy technique, a laser which has a large number of resonator modes, or natural output frequencies in laser emission, may be used. The missing or suppressed lines in the output spectrum can be indicative of the nature of the absorbing substance located in the resonator region of the laser.

In the instrument described above, the box 10 containing the super-toroidal conductors may be equivalent to the resonator region of a laser. As a result, in the absence of any absorbing material located in the box, it can be expected that the closed loop comprising the windings in the box and the rf amplifier 36 will cause resonant oscillation at a larger number of frequencies over the frequency range for which the amplifier 36 has sufficient gain. The different frequencies of resonance correspond to a multiplicity of resonant modes within the box, in combination with the phase delays represented by the leads to and from the rf amplifier 36 together with delays in the amplifier itself. Therefore it also can be expected that the material located in the box will cause a change in the pattern of the resonant oscillation frequencies due to the phase delay in the material. Nonlinearities in the loop may also cause, through redistribution of the energy circulating in the loop, appearance of new spectral components as a reaction to the suppression of other spectral components or/and shift of their frequencies.

Importantly, the super-toroidal windings of the conductors within the box 10 can operate over a very broad frequency band, since the length of wire in any one super-toroidal winding may be many times the free space wavelength of the relevant frequency. For example, the length of wire in a first order super-toroidal winding having a diameter (of the toroidal former itself) of say 10 cms may be 20 meters or more. The length of wire in similarly sized super-toroidal windings of third order may be several hundred meters. Thus, the length of wire in a super-toroidal winding in the instrument may be several times the free space wavelengths for frequencies above about 5 Mhz.

The super-toroidal windings of the conductors within the box 10 can operate over a very broad frequency band, because, due to the complexity of the winding the super-toroidal antennas have remarkably low inductances and capacitances at high frequencies.

As mentioned above, in the absence of a sample, the instrument illustrated would produce an output spectrum from feedthrough 38 to the spectrum analyzer 39 containing a large number of peaks over a wide frequency range. The presence of a sample in a container on the sample tray 28 within the instrument is believed to change the output spectrum from the instrument.

Importantly also, interaction with a sample within the instrument is not solely dependent on the electric dipole mechanism of absorption. Hitherto, conventional radio frequency spectroscopy has depended upon the effect of the incident radio frequency energy on dipoles formed by the molecules of the sample. Whereas some molecules are significantly dipolar (including water) many other molecules exhibit substantially no dipole moment so that they are substantially unaffected by homogeneous electromagnetic fields.

The super-toroidal windings used in the above instrument, when energized at frequencies greater than 2c/l, where l is the length of wire in a super-toroidal winding, generate electromagnetic fields which are strongly spatial inhomogeneous, at least in the near field region close to the torus of the winding. Where as a quadrupolar molecule, for example, is substantially unaffected by a dipole field, such a molecule can be rotated (excited) by a strongly inhomogeneous magnetic and electric fields. Importantly, some molecules may have no electric dipolar moment, or not only dipolar moment, but also show electric and magnetic multipolar moments which interact with strongly inhomogeneous electric and magnetic fields created within the device.

When operating at relatively high frequency, the super-toroidal windings used in the above instrument can generate highly inhomogeneous fields which should be absorbed/refracted in samples comprising molecules with electric and magnetic multipolar moments.

In this way, liquid samples which would produce only uninformative broad radio frequency absorption spectra in purely dipole electromagnetic fields, can produce much more informative absorption spectra in the strongly spatially inhomogeneous fields generated in the instrument described above.

Figure 9:
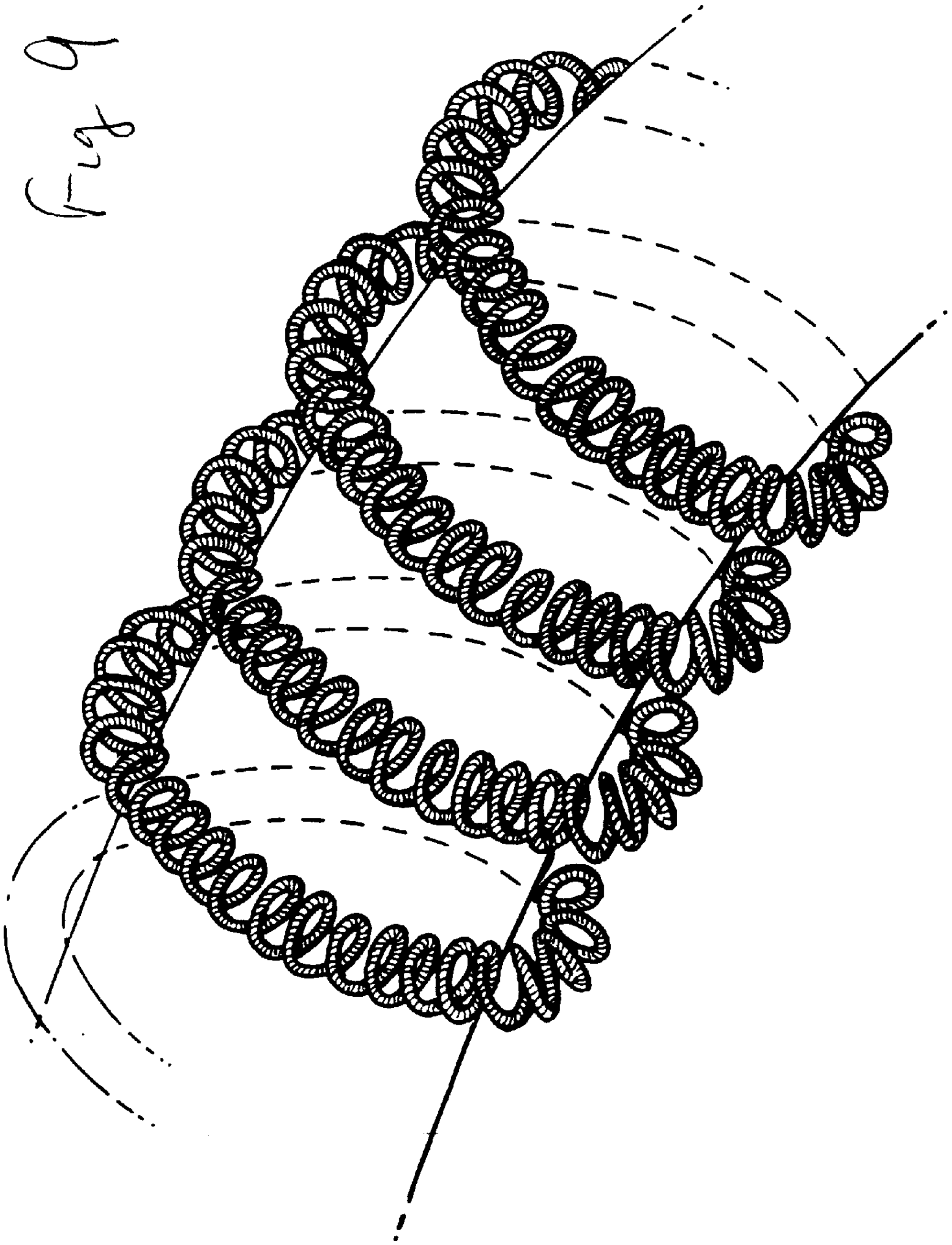
FIG. 9 is a circuit diagram illustrating the connections of the windings of a combined analysis and treatment apparatus.

A desired specimen may be treated by exposing the specimen to the electromagnetic fields generated by super-toroidal windings in an enclosure similar to that described above with reference to FIG. 3. Referring to FIG. 9, for treatment of a specimen, a second enclosure, here shown schematically at 40 is connected to the enclosure 10 as illustrated. The second enclosure 40 may have the identical components as described above for the sample analyzer enclosure and illustrated in FIG. 3. In the treatment enclosure 40, the left hand super-toroidal assembly (corresponding to assembly 20 in enclosure 10) is formed by an outer third order super-toroidal winding L7 on an inner second order super-toroidal winding L8. Similarly, the right hand super-toroidal assembly (corresponding to assembly 21 in the enclosure 10) is formed of a third order super-toroidal winding L12 on a second order super-toroidal winding L11. The super toroidal windings L9 and L10 correspond to the windings L3 and L4 of the enclosure 10.

The enclosure 40 for treatment of a specimen further includes conductive foil plates 41 and 42 on opposite sides of the toroidal assembly comprising windings L7 and L8, and 43 and 44 on opposite sides of the toroidal assembly comprising the windings L11 and L12. These plates are in fact illustrated in FIG. 3, but it should be understood that these plates are employed only in the enclosure used for treatment of a specimen and not in the enclosure used for sample analysis as first described with reference to FIG. 3. The conductive plates 41, 42 and 43, 44 may be made of flexible copper film and are annular in form having an inner radius similar to the inner radius of the super-toroidal assembly and an outer radius which is rather less than the outer radius of the super-toroidal assembly.

The pair of plates 41, 42 and 43, 44 function to couple energy capacitatively to the windings of the assembly located between the respective pairs, so that the windings may be energized more uniformly.

Referring to FIG. 9, the treatment enclosure is connected in circuit as illustrated. A broad band rf noise generator 45 produces pulses of broad band rf noise on an output line 46. The modulation may comprise pulses at either 1 Hz or 4 Hz repetition rate, with a duty cycle of 1:3. These pulses are used to modulate the wide band rf noise signal on line 46.

Figure 6:
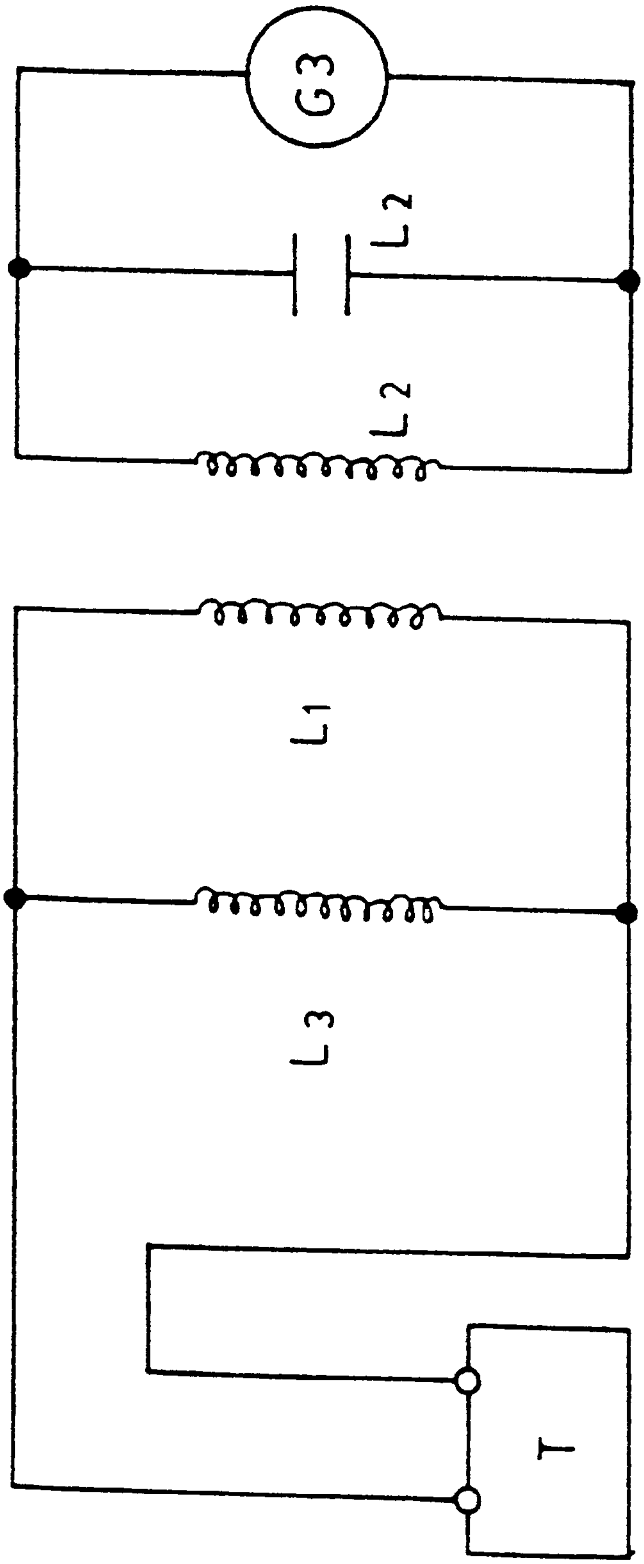
FIG. 6 is a circuit diagram illustrating how the windings in the enclosure of FIG. 3 may be connected together to provide sample analysis.

The outer third order and inner second order conductors L7 and L8 of the left hand super-toroidal assembly are connected in parallel with each other and with the inner second order and outer third order conductors L11 and L12 of the right hand assembly, and all together fed directly from the sample analysing enclosure 10. As can be seen, the signal from the sample analysing enclosure 10 which is supplied to the spectrum analyzer in FIG. 6 is, in the specimen treatment example illustrated in FIG. 9, fed to the windings L7, L8 and L11, L12 of the treatment enclosure 14.

The outer plate 41 and 43 on each of the super-toroidal assemblies is connected to ground and the inner plate 42 and 44 are supplied with the pulsed wide band rf noise signal on line 46 from the generator 45.

Signals from the remaining two super-toroidal windings L9 and L10 in the treatment enclosure 40 may be fed to a spectrum analyzer 48 for monitoring.

In operation, a specimen to be treated is located on the specimen tray (corresponding to the tray 28 of enclosure 10) in the treatment enclosure 40. A liquid sample is made up of the component in the specimen which is particularly to be treated and this sample is located on the tray 28 in the analyzer enclosure 10. The rf amplifier 36 is then energized to produce an rf spectrum on the line 49 from the analyzer chamber 10, which is in turn supplied to energize the windings L7, L8 and L11, L12 in the treatment chamber 40. At the same time, the generator 45 is energized to apply modulated wide band noise to the windings by capacitative coupling.

It has been observed that this process can provide effective treatment of the designated component of the specimen located in the treatment chamber 40. If the generator 45 is selected to produce pulses of wide band rf noise at 1 Hz, the treatment appears to be beneficial to the designated component of the specimen, so that if the component is a living organism, growth of the organism in the specimen is promoted. However, if the wide band rf noise applied by the generator 45 is modulated at 4 Hz, then the treatment is deleterious to the designated component, with the effect that the component can be destroyed or inactivated in the specimen.

Treatment has been performed of biological samples whereby only selected biological components of the sample have been effected by the treatment with no apparent effects on the remaining components of the sample.

Apparatus using super-toroidal windings was used in an experiment for the treatment in vitro of cells chronically infected with HIV-1. Samples were made up for the analyzer enclosure comprising p24 antigen, p120 antigen (proteins contained in HIV virus) and also genetically engineered pro viral HIV DNA.

Treatment specimens were then also made up.

The samples treated were:

1) Non infected cells including fresh peripheral white blood cells and human T-cells.

2) Chronically HIV-1 infected cells.

For treatment of the different specimens selected samples were located in an analyzer chamber and the equipment was energized as described above.

For the treatment of non-infected cells these were counted before exposure and treatment in the apparatus and then treated cells as well as a non-treated control set of cells were counted every other day for the following two weeks. The treated cells were exposed in the apparatus twice for 30 minutes with the rf noise generator providing pulses at 1 Hz and twice for 30 minutes with the generator providing pulses at 4 Hz. This was repeated during the following two days.

Subsequently cells were counted over the next two weeks and the cell count revealed that there was no difference in the growth rate of either the exposed fresh white blood cell cultures or the T-cell line when compared with cultures which had not been treated.

For chronically HIV infected cells, these were exposed for one hour to emissions generated by a sample of p24 antigen only located in the sample analyzer chamber, and subsequently for a total of two hours with only gp 120 antigen located in the sample analyzer chamber. Both treatments were conducted with the generator 45 providing pulses at 4 Hz. This treatment was repeated during the following four days and the cells were then counted. There was no difference in the growth rate of the exposed cells when compared with those which had not been treated.

Five days after the treatment, the cell suspensions of the treated and non treated chronically infected cells were spun separately at 1500 rpm for ten minutes. The supernatant was collected separately, followed by a serial ten-fold dilution and titration for virus yield in the non infected T-cells, which are highly susceptible to the HIV-1 strain used. Following titration, the cell culture was monitored for cytopathic effect (CPE) over the following ten days. It was then established that while the HIV-1 yield in the non exposed cell culture fluid was $10^6$ infectious particle per ml, in the fluid of the exposed cells there was only a yield of $10^5$ infectious particles per ml. Thus, treatment for chronically infected cells had led to ten-fold reduction in HIV-1 yield of the chronically infected cells.

In a further procedure, cells which were acutely infected with HIV-1 were also exposed twice for 30 minutes with each of p24 antigen and gp 120 antigen in the sample analyzer chamber, with the rf noise generator providing pulses at 4 Hz, followed by a further exposure each for 45 minutes again at 4 Hz. This exposure was repeated over a three day period both with HIV-1 infected non exposed T-cells as well as T-cells which were exposed before the acute infection. Thereafter the HIV-1 infected and exposed cell culture as well as to control non exposed HIV-1 infected cell cultures were pipetted forcefully to disrupt the infected cells in order to maximise HIV-1 release into the fluid. This was followed by centrifugation at 1500 rpm for 10 minutes and the supernatant from each cell culture was then separated. Virus titration with ten-fold dilution followed. The two non exposed HIV-1 infected cultures were found to contain $10^6$ HIV-1 infectious particles per ml, while in the fluid of the exposed culture there was only $10^4$ HIV-1 infectious particles per ml. Thus, there was a 100-fold reduction in the virus yield. One of the two cell cultures which were not treated in the above process was previously treated in the apparatus prior to infection. However, the culture treated prior to infection, and not treated after infection, had a similar infectious particle count as the infected cultures which had not been treated either before or after infection. Thus, treatment prior to infection, does not reduce the rate of HIV-1 production.

Alternative Embodiments

Figure 10:
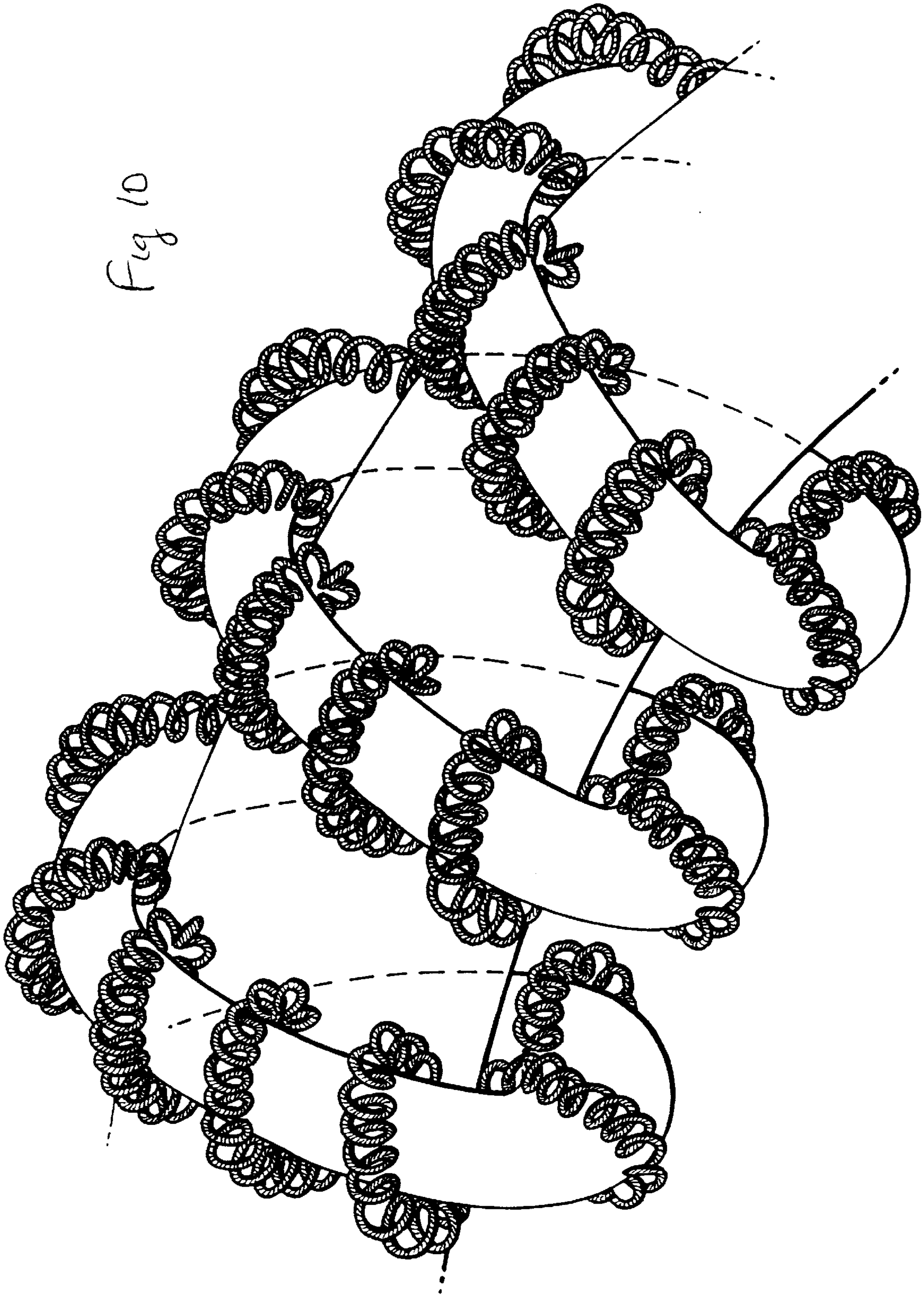
FIG. 10 is a view in elevation of the interior of an alternative form of the present invention.
Figure 11:
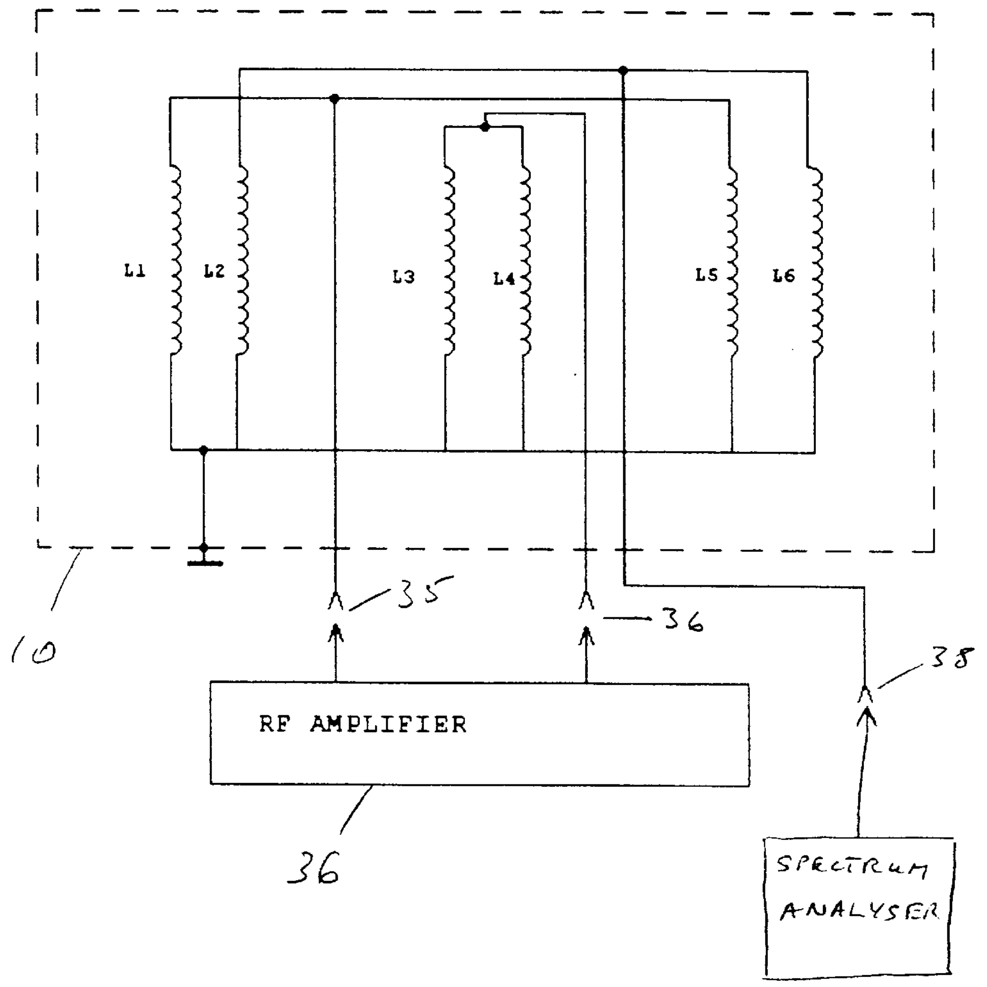
FIG. 11 illustrates the super-toroidal winding assembly used in the assembly of FIG. 10.
Figure 12A:
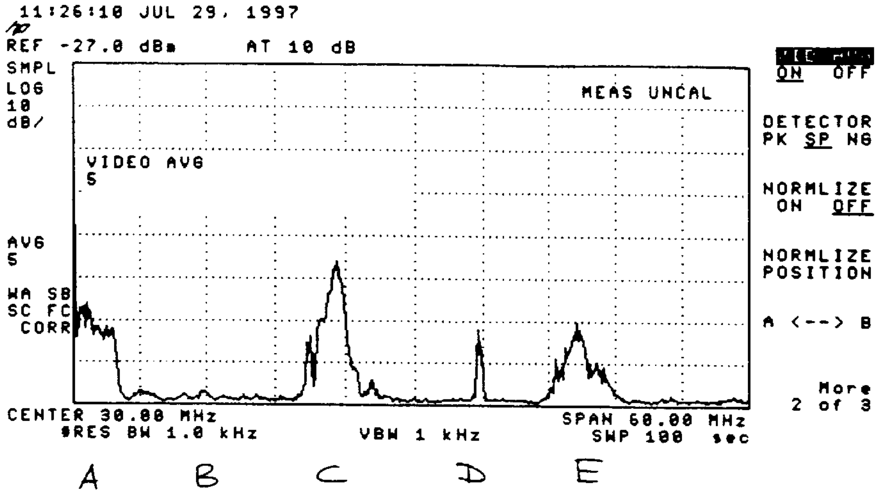
FIG. 12 is a circuit diagram illustrating how the components of the embodiment of FIG. 10 are connected in a treatment application.
Figure 12B:
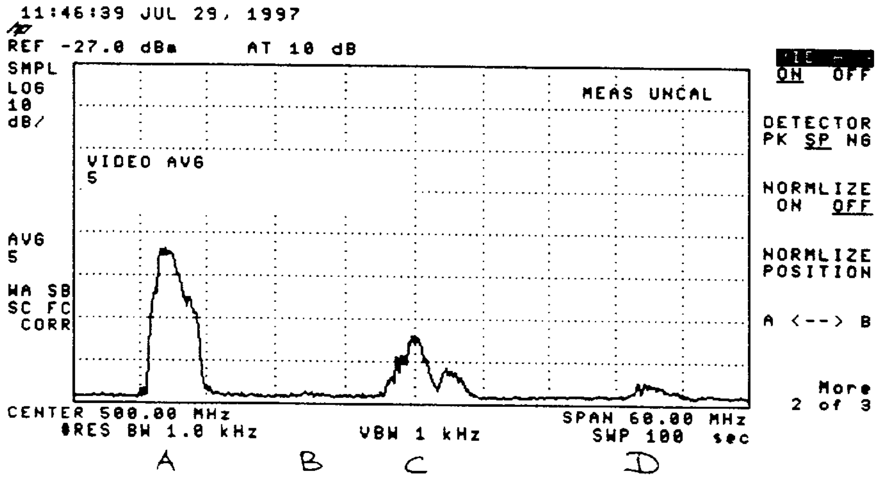
Figure 13A:
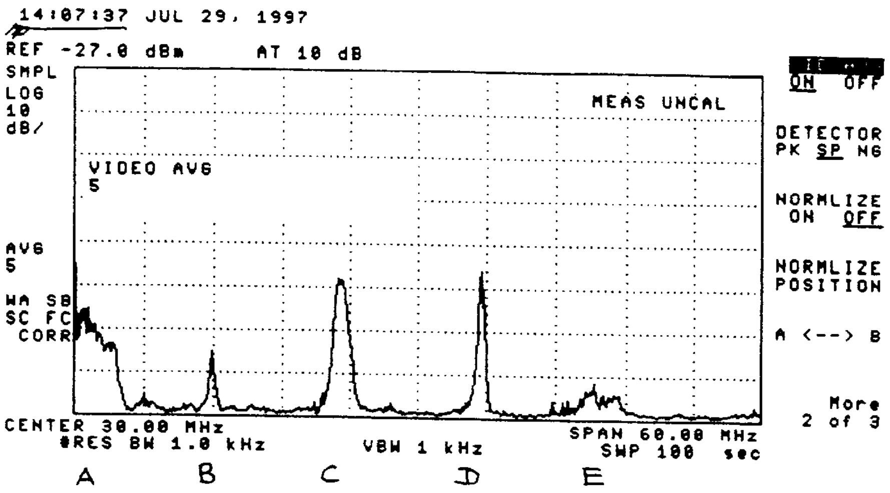
Figure 13B:
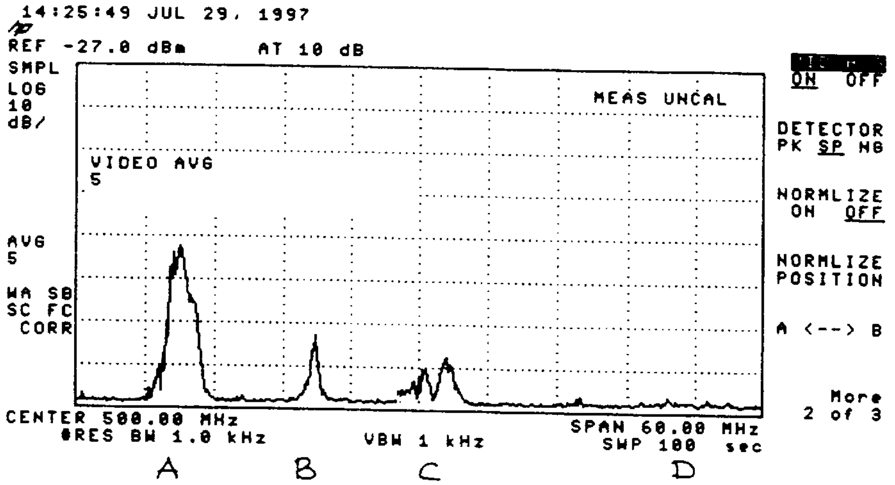
Figure 14:
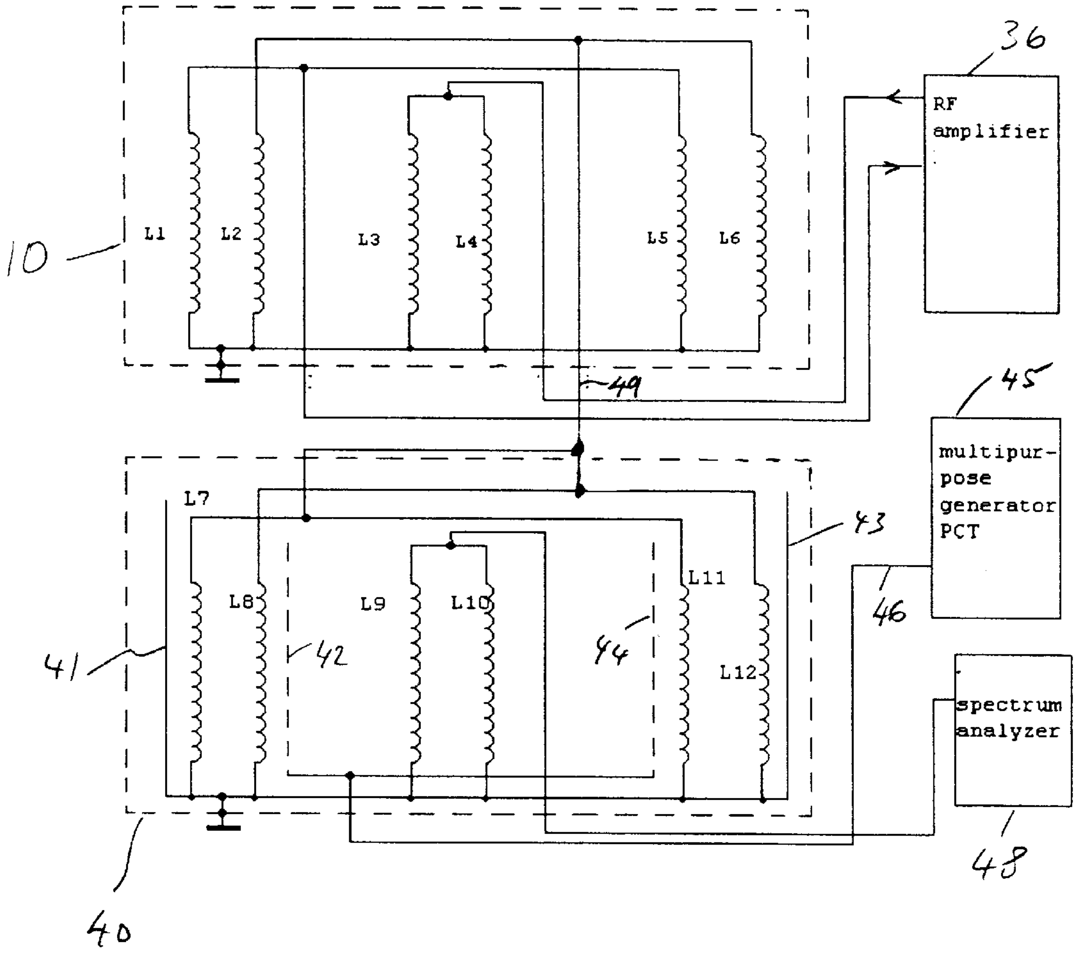

Other embodiments of the apparatus described above can be contemplated. FIGS. 10, 11 and 12 illustrate an embodiment of apparatus which can be used for the treatment of specimens externally of a screened container. In FIG. 10 a super-toroidal assembly 50 is located against a front wall 51 of a container. The container comprises rear and bottom walls 52 and 53 made of metal, and upper and front walls 54 and 51 made of dielectric material. The super-toroidal assembly 50 is located against the front wall 51 by means of a dielectric retaining plate 55. The assembly 50 is secured between the plate 55 and the wall 51 by dielectric foam material 56 and 57. A single wire helical antenna 58 is also mounted within the enclosure on the front wall 52. A feedthrough 59 enables radio frequency energy to be supplied to the helical antenna 58. Connections to the super-toroidal conductor assembly 50 are provided through side walls of the container which are not illustrated in FIG. 10. The side walls (parallel to the plane of the paper) are also made of dielectric material.

Figure 15:
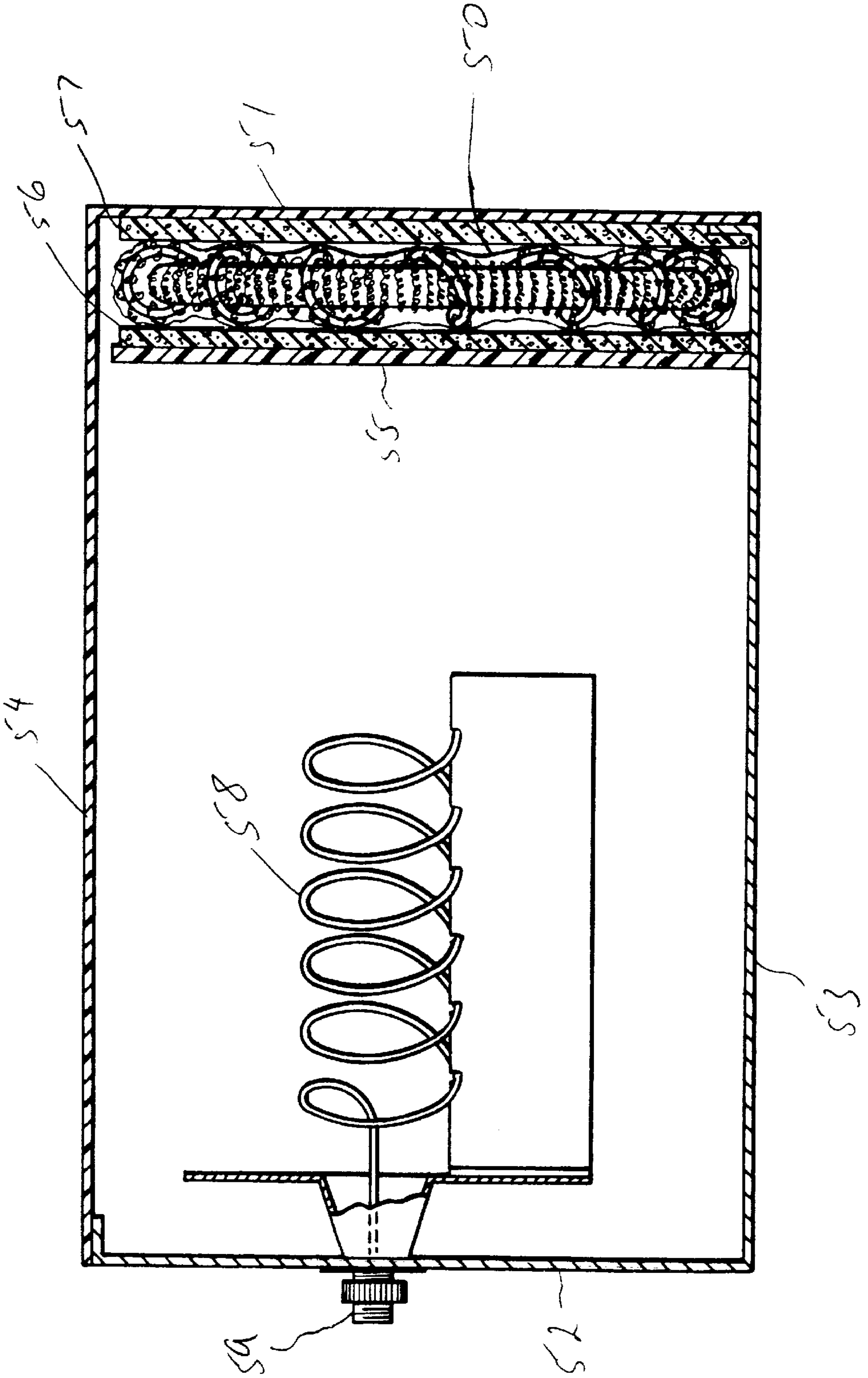
Figure 16:
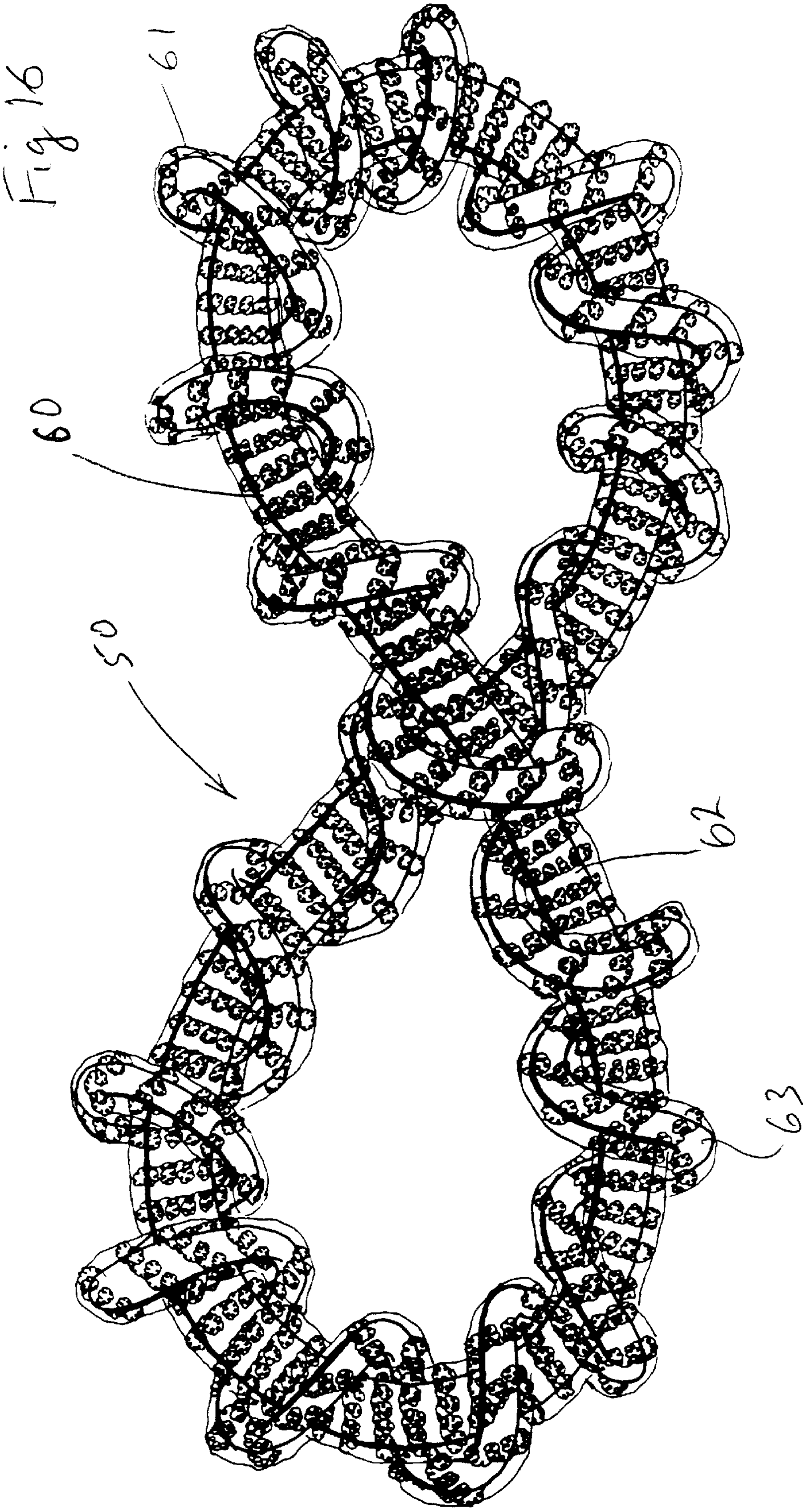
Figure 17:
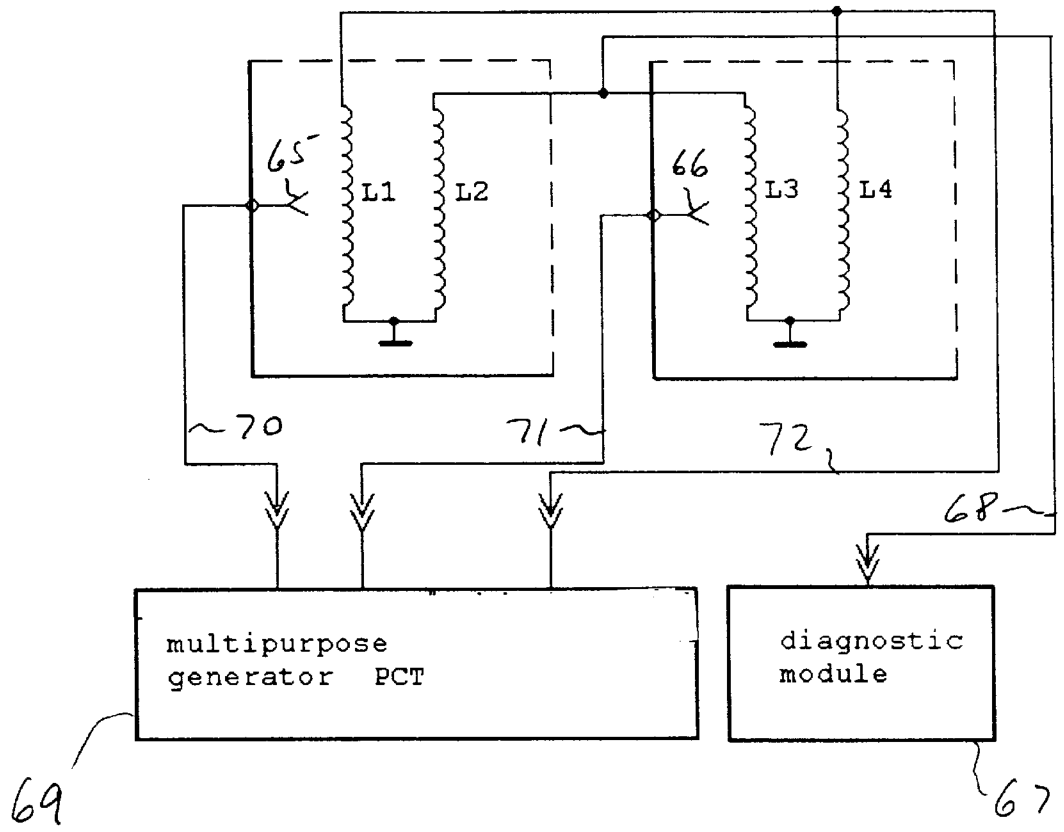

FIG. 11 illustrates the form of the super-toroidal conductor assembly 50 shown in FIG. 10. The assembly 50 comprises a second order super-toroidal winding which forms the toroidal former for a third order super-toroidal winding 61. The toroidal former 62 of the second order winding 60, and the helical former 63 of the third order winding 61 are themselves sufficiently flexible to allow the assembly 50 to be twisted into a figure of eight as illustrated in the drawing. This figure of eight arrangement is then mounted in the container illustrated in FIG. 15 against the front wall 51 as described above. Separate connections can be made to the inner second order and the outer third order toroidal windings of the assembly 50.

For treatment of an external body, for example, two treatment assemblies such as illustrated in FIG. 10 may be used, e.g. by placing one on opposite sides of the body to be treated, with the body located between respective front faces 51 of the treatment assemblies.

FIG. 12 illustrates the electrical connections for the elements in the treatment assemblies, with L1 and L2 representing the inner second order and outer third order toroidal windings of the toroidal assembly in one container, and L3 and L4 representing respectively the inner second order and outer third order windings of the other container. The helical antenna 58 in each treatment container is represented in FIG. 12 at 65 and 66 for the two containers respectively.

Figure 7:
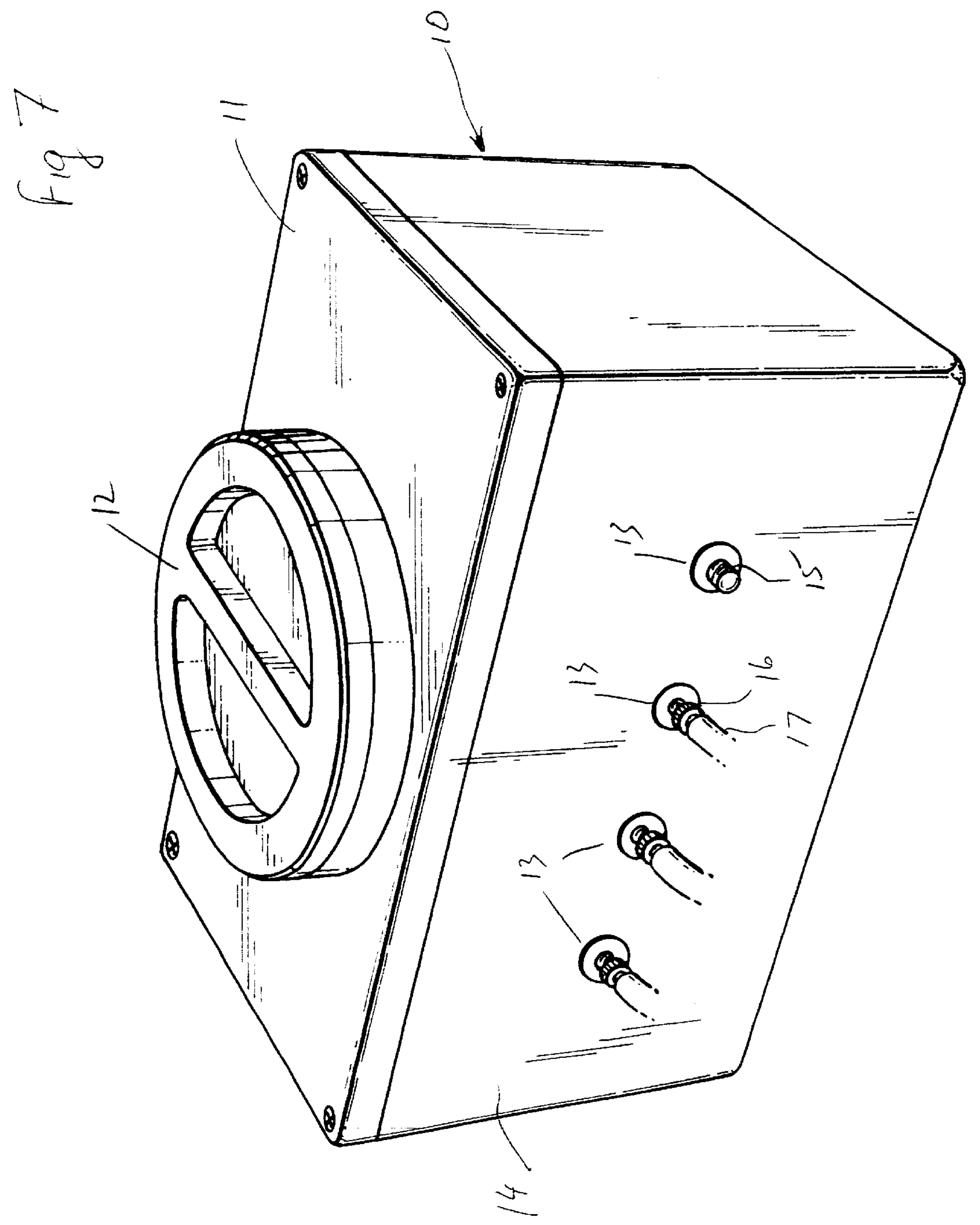
FIGS. 7*a* and 7*b* are graphical representations of radio frequency spectra obtained for a sample of distilled water at different center frequencies.

The outer third order winding L2 of one assembly and the inner second order winding L3 of the other assembly are connected together in parallel and supplied with the rf spectrum signal generated by an analyzer assembly such as illustrated in FIG. 7. Thus, the Diagnostic Module 67 illustrated in FIG. 12 may be constituted by a sample analyzer assembly as described with reference to FIG. 6 and as illustrated in the upper part of FIG. 9. The signal supplied by the Diagnostic Module 67 on line 68 in FIG. 10 corresponds to the signal supplied via feedthrough 38 to the spectrum analyzer in FIG. 6, and the signal supplied along lines 49 to the treatment chamber 40 in FIG. 9.

The wide band rf noise generator 69, corresponding to generator 45 described with reference to FIG. 9, provides a pulsed wide band rf noise signal on lines 70 and 71 to each of the helical antennae 65 and 66. The rf noise signal on each of lines 70 and 71 may be pulsed at 1 Hz or 4 Hz as described above. Preferably, the pulses on line 71 are phased to occur during the spaces between pulses on line 70. The pulse signal itself is supplied from the generator 69 on line 72 directly to windings L2 and L3 in parallel.

The above apparatus has been found effective in the treatment of relatively larger bodies of material. As before, a sample of the component which is to be specifically treated in the body is prepared and placed in the sample analyzer enclosure. The apparatus is then activated with the body to be treated located between the super-toroidal assemblies 50 of the two treatment units shown in FIG. 12.

In the above described embodiments, an rf spectrum is obtained from a sample analyzer, by the use of an rf resonator comprising a high gain wide band rf amplifier feeding output and input windings in a resonator region. Instead, a wide band signal could be generated externally of the sample analyzer chamber and fed to one or more super-toroidal winding within the chamber. A second sensing winding or windings would then be used to monitor the effect on the electromagnetic field produced by the first winding by a sample to be analysed. For example, the externally generated wide band rf signal might comprise a series of relatively closely spaced rf frequencies, and the detection arrangement could monitor changes in amplitude of these rf frequencies as a result of the presence within the electromagnetic field generated of a sample to be analysed.

In another arrangement, a single super-toroidal winding could be used, energized by an externally generated rf signal. The impedance of the super-toroidal winding could then be monitored and changes in that impedance detected resulting from the presence within the electromagnetic field generated by the winding of a sample to be analysed.

Although the super-toroidal winding could be supplied with a wide band rf signal comprising a range of frequencies simultaneously, instead the antenna could be energized at a single rf frequency which is swept over a desired band. Alternatively, a predetermined selection of rf frequencies could be generated one after the other and supplied to the super-toroidal winding.

A further method of energizing the super-toroidal winding would be to apply a pulse to the winding and monitor modifications to the frequency content of the resulting electromagnetic field due to the presence in the field of a sample to be analysed. It will be understood that a short duration pulse (impulse) is in effect a wide band signal.

In the above described examples, super-toroidal windings are energized by direct connection of rf signals across the ends of the windings. Instead, any other method could be used for energizing the windings, including multi-terminal connections, capacitive links, inductive links etc.

Although an example is described above of an application of the treatment process of the invention to the treatment of HIV-1 in vitro, the invention may also be applicable to in vivo treatment.

A large scale chamber has been constructed containing super-toroidal windings as discussed above, with the chamber being large enough to accommodate a human being. By energizing the super-toroidal windings in the chamber with radio frequency signals having spectral content determined by a sample analyzer, e.g. of the kind described above with reference to FIG. 11, it has proved possible to treat an entire human patient and substantially reduce, if not eliminate infection, specifically including HIV-1.

What is claimed is:

1. A method of treatment of a living organism comprising the steps of generating a strongly spatial inhomogeneous oscillating electric and magnetic fields, and exposing the living organism to said electric and magnetic fields for treatment.

2. A method as claimed in claim 1 wherein the electric and magnetic fields have a frequency content selected to be specific to the living organism to be treated.

3. A method as claimed in claim 1 wherein the field is generated by energising a super-toroidal winding with a frequency which is high relative to 2c/l, where c is the speed of light in free space and 1 is the length of wire in the super-toroidal winding.

4. A method according to claim 1 wherein the fields are created by two periodic signals, one signal being within the band from one kilocycle to 1000 gigacycles per second, and being modulated by the second periodic signal which is a low frequency signal within the band of from 0.001 to 100 cycles per second.

5. A method according to claim 4, wherein the low frequency sinusoidal signal is chopped at a phase angle of $0.33\times2\pi$ to produce a stimulating effect.

6. A method according to claim 4, wherein the low frequency sinusoidal signal is chopped at a phase angle of $0.25\times2\pi$ to produce an inhibiting effect.

* * * * *